United States Patent
Jarva (10) Patent No.: US 9,622,716 B2
(45) Date of Patent: Apr. 18, 2017

(54) ARM STRUCTURE FOR INTRA-ORAL X-RAY DEVICE

(75) Inventor: Mikko Jarva, Helsinki (FI)

(73) Assignee: PLANMECA OY, Helsinki (FI)

( * ) Notice: Subject to any disclaimer, the term of this patent is extended or adjusted under 35 U.S.C. 154(b) by 0 days.

(21) Appl. No.: 14/006,431

(22) PCT Filed: Mar. 21, 2012

(86) PCT No.: PCT/FI2012/050287
§ 371 (c)(1),
(2), (4) Date: Sep. 20, 2013

(87) PCT Pub. No.: WO2012/127116
PCT Pub. Date: Sep. 27, 2012

(65) Prior Publication Data
US 2014/0011156 A1   Jan. 9, 2014

(30) Foreign Application Priority Data
Mar. 21, 2011   (FI) ...................................... 20110102

(51) Int. Cl.
| A61B 19/00 | (2006.01) |
| A61B 17/00 | (2006.01) |
| F16M 11/00 | (2006.01) |
| A61B 6/14 | (2006.01) |
| A61B 6/00 | (2006.01) |
| F16M 11/08 | (2006.01) |
| F16M 11/20 | (2006.01) |
| F16M 13/02 | (2006.01) |
| F16M 11/06 | (2006.01) |

(52) U.S. Cl.
CPC .............. *A61B 6/145* (2013.01); *A61B 6/14* (2013.01); *A61B 6/4452* (2013.01); *F16M 11/08* (2013.01); *F16M 11/2021* (2013.01); *F16M 11/2092* (2013.01); *F16M 13/02* (2013.01); *A61B 6/4423* (2013.01); *F16M 11/06* (2013.01); *F16M 2200/044* (2013.01); *F16M 2200/048* (2013.01); *F16M 2200/065* (2013.01); *F16M 2200/068* (2013.01)

(58) Field of Classification Search
CPC .......... F16M 1/04; F16M 11/06; F16M 11/10; F16M 11/2014; F16M 2200/06; A61B 17/00; A61B 19/00; A47B 2200/0088
USPC ......... 248/274.1, 276.1, 278.1, 284.1, 281.1, 248/317, 919; 600/102
See application file for complete search history.

(56) References Cited

U.S. PATENT DOCUMENTS

| 4,545,555 A | * | 10/1985 | Koch ........................ 248/280.11 |
| 5,779,209 A | * | 7/1998 | Rello .......................... 248/278.1 |
| 6,837,468 B1 | * | 1/2005 | Kantor et al. ............. 248/278.1 |

(Continued)

FOREIGN PATENT DOCUMENTS

EP   1 520 548 A2   4/2005

Primary Examiner — Tan Le
(74) Attorney, Agent, or Firm — Fay Sharpe LLP (57) ABSTRACT

An arm construction of an intra-oral x-ray device according to the present invention comprises at least two elongated support arms (55, 56, 55', 56') jointed to each other, into connection with a substantially first end of the first support arm (55) of which is arranged a radiation source (4) and in which the jointing between the support arms is implemented such that the successive support arms (55, 56, 55', 56') connect to each other from sides (68, 69) of the support arms facing each other.

19 Claims, 5 Drawing Sheets

(56) References Cited

U.S. PATENT DOCUMENTS

| | | | |
|---|---|---|---|
| 7,100,880 B2* | 9/2006 | Oddsen, Jr. | 248/278.1 |
| 7,243,892 B2* | 7/2007 | Pfister | 248/919 |
| 8,191,487 B2* | 6/2012 | Theesfeld et al. | 108/144.11 |
| 8,205,847 B2* | 6/2012 | Dorris et al. | 248/317 |
| 8,424,833 B2* | 4/2013 | Muller | F16M 11/04 |
| | | | 248/324 |
| 9,022,339 B2* | 5/2015 | Borg | H02G 7/05 |
| | | | 248/323 |

* cited by examiner

ARM STRUCTURE FOR INTRA-ORAL X-RAY DEVICE

FIELD OF INVENTION

The invention relates to an arm structure for an intra-oral, x-ray device used in connection with intra-oral x-ray imaging.

BACKGROUND OF INVENTION

Dental intra-oral x-ray images are taken by using x-ray examination devices which typically include, on the one hand, a multi-jointed arm construction and a radiation source arranged in connection with it and, on the other hand, an image-data receiving means, such as a film or an electric imaging sensor, to be positioned within the patient's mouth in a desired orientation. Typically, to a cover of the x-ray source is attached or arranged attachable an elongated collimator structure to limit an x-ray beam to the image-data receiving means and thus minimise the radiation dose received by the patient. The imaging process includes placing the x-ray device in the proximity of the object area to be imaged and aiming the x-ray beam such that it will meet the sensor in a correct orientation and at a desired angle. Typically, the beam is positioned perpendicularly with respect to the image-data receiver arranged inside the patient's mouth.

One typical intra-oral x-ray device according to prior art is described in patent specification FI 119008. The device includes, as shown in attached FIGS. 1-4, a control panel 2, a jointed 8, 9 arm construction 3 consisting of several arm parts 5, 6, 7 and an x-ray source 4. The centre axes of the arm parts define a plane where the arm parts 5, 6 can be turned with respect to virtual joint axes defined by the jointings 8, 9. The x-ray source 4 is connected substantially to an end of the furthest arm part 5 by a structure 10 and 11, which enables turning the x-ray source with respect to both a vertical and a horizontal axis. The control panel 2 is attached to a horizontal arm 7 supporting the outermost arm parts 5, 6 of the arm construction.

Patent specification US2007/0237291 describes an arrangement in which an arm construction supporting a radiation source is arranged into connection with a dental care apparatus.

Typically, an electricity and signal cabling related to the use of the radiation source has been arranged routed through the arrn construction of the intra-oral x-ray device. Furthermore, the arm construction must be balanced in. one way or the other, in order to be able to move the arms more lightly and, additionally, in order the radiation source staying at a desired position also otherwise than by holding it. This typically means arranging springs within the arms. The arm parts are typically hollow pieces manufactured of rigid material. Pulling the cables though such arms when assembling the arm construction is awkward, as is setting the springs within such elongated hollow structures. In many arrangements, the arm construction has not been covered at the point of the jointing, whereby the cables left unprotected are prone to damages and otherwise to wear within this area, due to forces which are applied to them when turning the arm construction into different positions.

BRIEF DESCRIPTION OF INVENTION

The object of the invention is to create new solutions relating to the problem field described above, such as to provide a novel type of an arm construction for an intra-oral x-ray device the assembly and maintenance of which are relatively easy, or in which the wear of cables can be decreased, or in which the hygiene can be improved by minimising the number of components visible and, on the other hand, of surfaces difficult to keep clean.

The object of the invention is achieved by the arm construction according to the claims attached. Due to the invention and its various embodiments, the cabling routed through the arm construction is not repeatedly susceptible to forces induced by the cables bending into different positions. On the other hand, the cables and balancing springs to be placed within the arm construction are easy to install and, if required, also to replace, as there is no need to disassemble the arm construction as a whole for these maintenance measures. The arm construction can be implemented by almost or totally identical arm parts, the number of components to be used needs not to be large, and the whole structure can be implemented as covered which facilitates its cleansing. The arm construction is preferably arranged to support the radiation source of the intra-oral x-ray device to enable adjusting at least the height position of the radiation source, i.e. to comprise a structure in which the pivot axis between the arm parts are horizontal. The arm structure as a whole may be attached to a horizontal arm to increase the range of movement of the arm structure, but also e.g. directly to a wall or a ceiling.

Next, the invention, some of its preferable embodiments and advantages achievable by them will be described in more detail and also with reference to the enclosed figures.

DETAILED DESCRIPTION OF INVENTION

FIGS. 5-8 illustrate the structures of an arm construction of an intra-oral x-ray device according to the invention. A base 53 of the arm construction consists of two jointed elongated support arms 55 and 56, of which, the arm supporting a radiation source 4 is also referred to here as the first support arm 55. Ends of the support arms 55, 56 to be connected together are set side by side and they are attached to each other such that the first support arm 55 supporting the radiation source 4 can turn with respect to a rotation axis 60 passing through the jointing point, the rotation axis 60 orientating perpendicularly with respect to the centre axes of the support arms 55, 56. Thus, the first support arm 55 supporting the radiation source 4 is movable on a plane which is parallel with but at a distance from a plane, which is defined by the centre axis of the second support arm 56 and an axis intersecting it and being at right angles to said rotation axis 60.

When also the end of the second support arm 56 opposite with respect to the above-described jointing is arranged turnable with respect to a rotation axis parallel with the above-described rotation axis 60, the support arms 55, 56 can be turned on planes parallel and next to each other to change the length and orientation of the arm construction 53 and, thus, location of the radiation source 4 along the plane of motion of the first arm part 55.

The actual joint structure can be implemented in many different ways within the scope of the basic idea of the invention. For instance, in the embodiment according to FIG. 6, the structure includes a sleeve-like spindle 66 which protrudes from the side surface of the second (the next) support arm 56 towards the side surface of the first support arm 55. To the first support arm 55 is arranged, again, a sleeve-like axle 62 or hole which is dimensioned with respect to said spindle 66 such that the spindle 66 can be attached to the structure from the opposite side of the first support arm 55 by a suitable attaching means 67, such as e.g. a nut.

Figure 1:
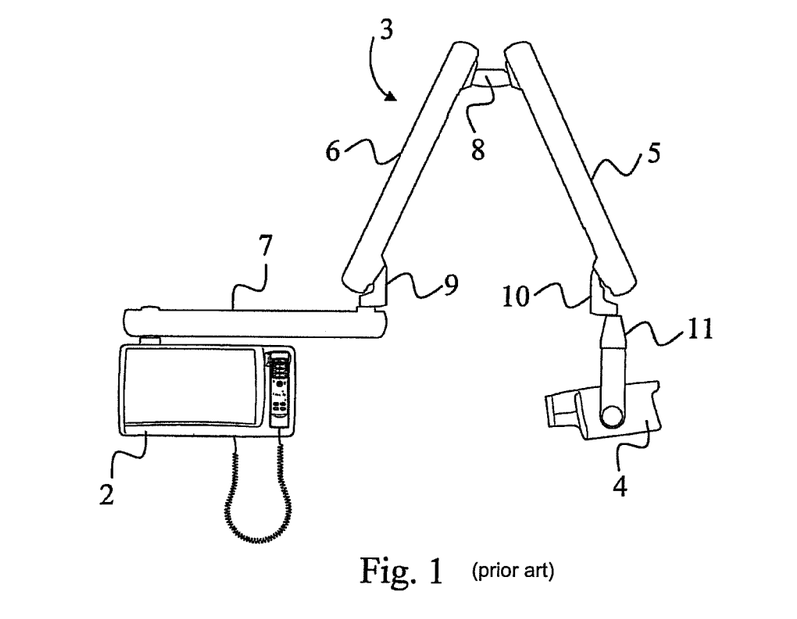
FIG. 1 is a side view of a typical intra-oral x-ray device according to prior art.
Figure 2:
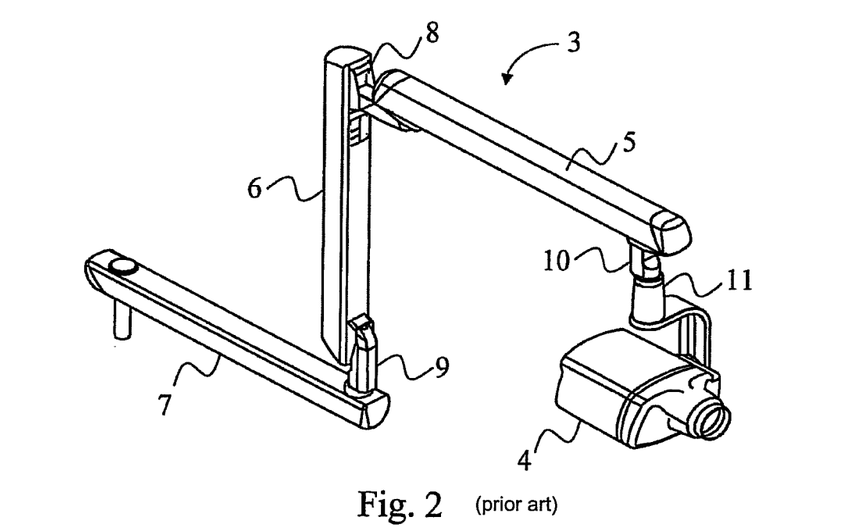
FIG. 2 is a perspective view of an arm construction of the device according to FIG. 1.
Figure 3:
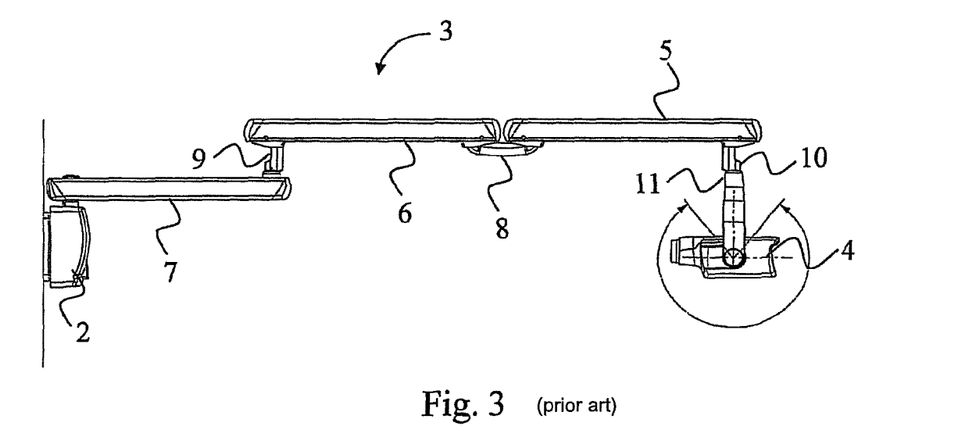
FIG. 3 is a side view of the device in FIG. 1, the arm construction being in its longest position.
Figure 4:
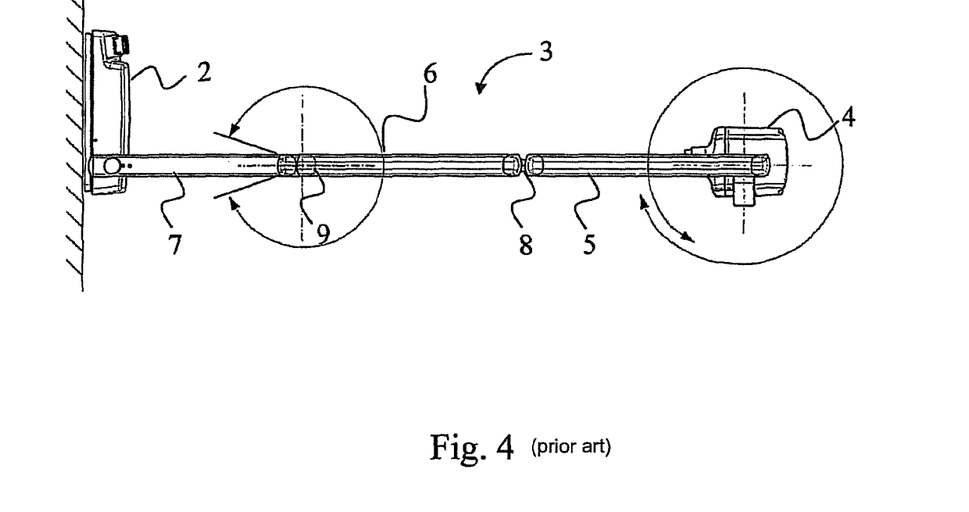
FIG. 4 is a top view of the device in FIG. 1, the arm construction being in its longest position.
Figure 5:
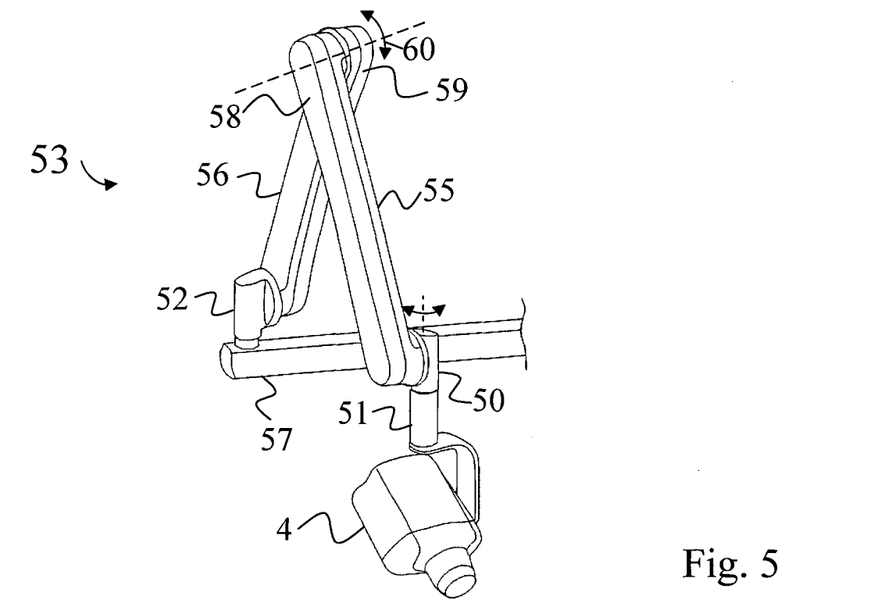
FIG. 5 is a perspective view of an arm construction according to one exemplar embodiment of the invention for an intra-oral x-ray device.
Figure 6:
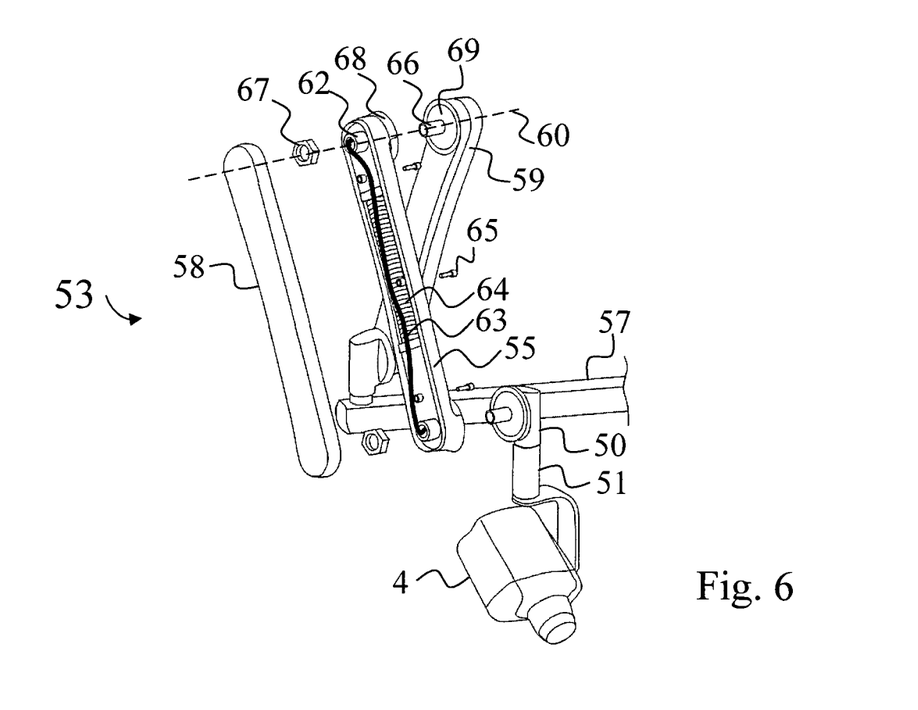
FIG. 6 is a perspective view of an arm construction according to one exemplar embodiment of the invention for an intra-oral x-ray device, as one of the arms opened.
Figure 7:
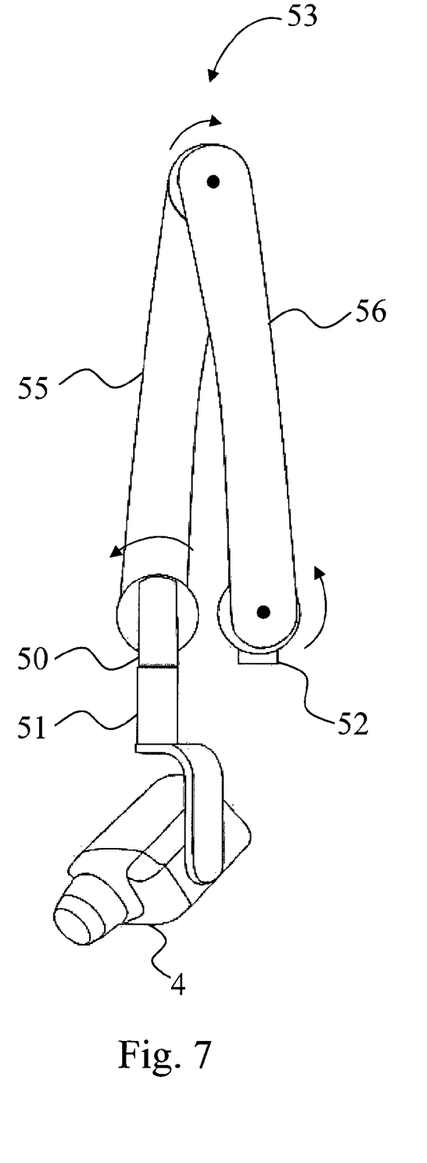
FIG. 7 is a side view of an arm construction according to one exemplar embodiment of the invention for an intra-oral x-ray device.
Figure 8:
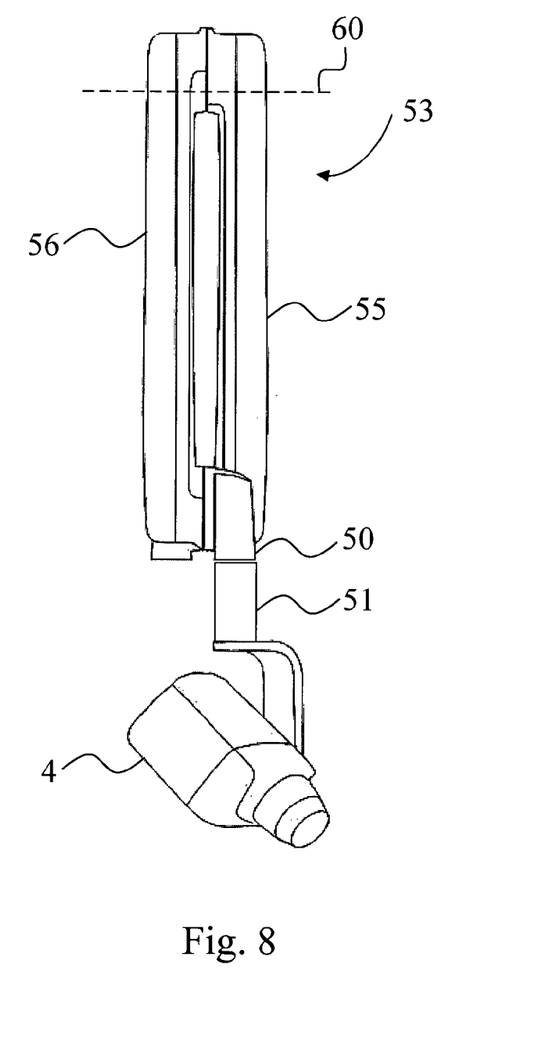
FIG. 8 is a front view of an arm construction according to one exemplar embodiment of the invention for an intra-oral x-ray device.

In the embodiments shown in FIGS. 5-7, structures 68, 69 of the support arms 55, 56 setting against each other are implemented as circular matching pairs which are arranged to set precisely against each other. In more general terms, this structure is preferably implemented by parts having a cross-section of the shape of a circle or part of a circular arch with substantially the same radius and being arranged to cover, when attached together, the joint structure used in each occasion. Then, when turning the support arms, no open gaps are formed where e.g. the user of the device could hurt his finger.

In the embodiments of the invention shown in the enclosed FIGS. 5-9, support structures 50, 51 of the x-ray source 4 are attached to the first support arm 55 by a structure similar to the one by which the support arms are attached to each other. Correspondingly, as shown in FIGS. 5-7, the arm part 56 jointed to the first arm part 55 is attached to an attaching structure 52 comprising a horizontal arm 57 supporting it by a structure similar to the one by which the support arms are attached to each other. Such an embodiment of the invention enables implementing the support arms 55, 56 as almost or completely identical structures, which is advantageous, inter alia, from the viewpoint of manufacturing costs and congruence of the assembly. The solution also makes it simple to implement the arm construction with a desired number of support arms 55, 56, 55', 56'.

In the embodiment according to FIGS. 5-7, identical structures 50, 52 are arranged as extensions of the first support arm 55 of the arm construction and of the furthest joint structure of the furthest support arm 56. They connect, on one hand, the radiation source 4 to the first support arm 55 and, on the other hand, the furthest support arm 56 to the horizontal arm 57 supporting the whole arm construction. This structure 50, 52 is arranged to enable a degree of freedom of motion with respect to an axis perpendicular to the rotation axis 60 between the support arms 55, 56.

In one preferable embodiment of the invention, the support arms 55, 56 are arranged longitudinally openable. This arrangement enables an easy access to the inner space of the support arms substantially for their length of the assembly which, inter alia, facilitates installation of springs 64 and cablings 63 to be arranged within the arms, used for balancing the arm construction. Then, also the maintenance measures can be performed without completely disassembling the arm construction. In the embodiment according to the enclosed figures, the support arms are implemented as two-piece in longitudinal direction such that jointing structures at both ends of the support arms are arranged to their first sides, whereby from the side opposite to this side is arranged detachable a cover piece 58 of the length of the whole arm part. In the case according to the enclosed figures, the cover piece 58 is arranged to be attached by a screw 65 and detachable as a whole, but the structure can also be implemented with some other kind of an attachment and also as an openable structure e.g. by means of hinging. The openable or detachable structure can also consist of more parts than one. An essential issue is that the openable or detachable section, or sections together, covers a significant portion of the length of the support arm such that installation and replacement of the cabling to be routed through the arm part, as well as the springs and other possible components to be arranged within the arm part, becomes substantially easier compared with a situation in which one has to perform measures through an open end of a hollow structure.

Regarding the cabling 63 transferring electric power or control signals or other information and arranged to be routed inside the support arms 55 and 56, the substantial advantages of the invention include the possibility to implement the cabling, at the jointings of the arm construction, as parallel with the rotation axis 60 between the support arms 55, 56. In the embodiment according to FIG. 6, the cabling is routed from one support arm to the other through the abovementioned sleeve-like pails and through an equivalent structure also to the radiation source 4 and, on the other hand, out of the arm construction according to the invention at its other furthest end. When one prior-art problem is the wear of the cabling as it passes parallel with the centre axes of the arm parts past the joint axes between the arm parts, whereby it falls under the stress of forces caused by turning of the arm parts, the routing of the cabling enabled by the invention offers a possibility to decrease stresses acting on the cabling. The arrangement also offers a natural chance to arrange the whole cabling as protected within the covers of the arm construction and thus protected from effects which could damage the cabling from the outside.

Furthermore, when successive support arms move in the construction according to the invention on planes substantially parallel but at a distance from each other, one can note the invention offering a possibility to implement the arm construction such that the first support arm 55 moves on a plane which is substantially parallel with a plane which is defined by the centre axis of the support arm 66 jointed to the first support arm 55 and an axis perpendicular with respect to said joint axes 60 and intersecting with said centre axis, which plane on which the first support arms 55 moves is at such a distance from this comparison plane that, when the first support arm 55 is turned to any angle with respect to the support arm 56 to which it is jointed, none of the structures of these successive support arms touch each other.

Figure 9:
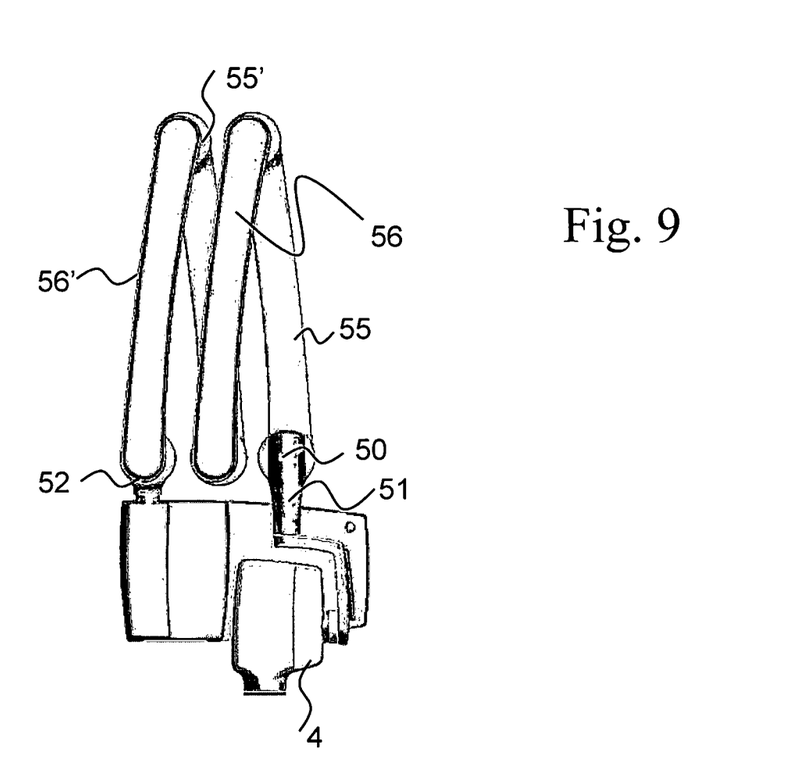
FIG. 9 is a side view of an arm construction according to a second exemplar embodiment of the invention for an intra-oral x-ray device.
Figure 10:
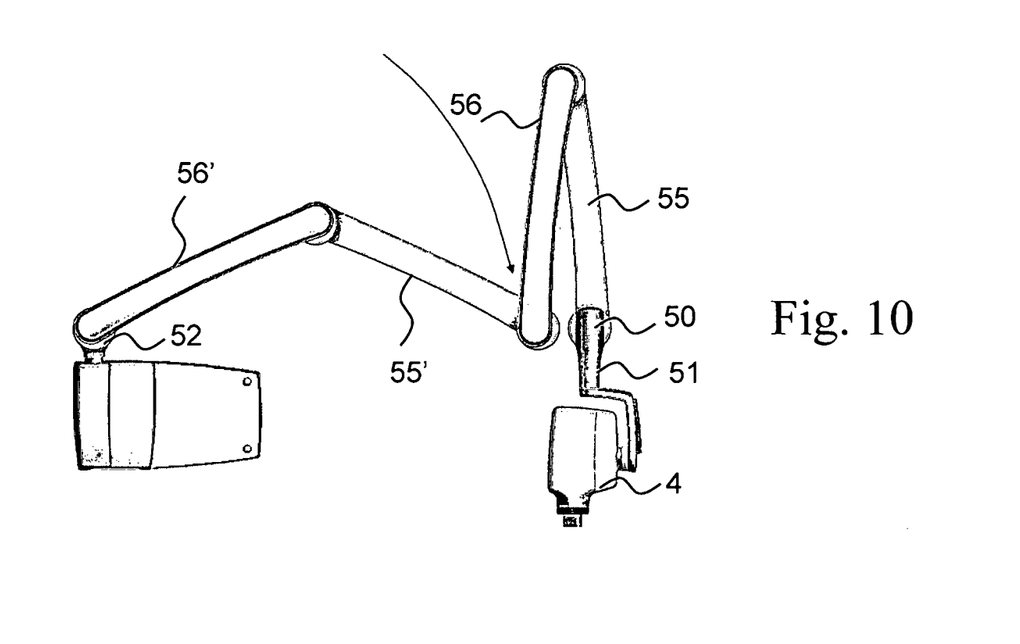
FIG. 10 is a side view of the arm construction according to FIG. 9, the arm construction being in a partly extended position.

FIGS. 9 and 10 illustrate an arm construction of an intra-oral x-ray device which includes four identical support arms 55, 56, 55' and 56'. The arm construction may be implemented of similar components as described in connection with FIGS. 5-8.

It is evident to those skilled in the art that the invention and its embodiments are not limited to the examples described above, but they may vary within the scope of the enclosed claims. Therefore, one could say that in the intra-oral x-ray device according to the invention, the arm construction of which comprises at least two elongated support arms 55, 56, 55', 56' jointed to each other, into connection with an end of the first support arm 55 of which and substantially opposite with respect to said jointing is arranged a radiation source 4 and which jointing is implemented such that the first support arm 55 is turnable with respect to a physical or virtual joint axis 60, which is defined by said jointing, said jointing can be preferably implemented such that the successive support arms 55, 56, 55', 56' are connected to each other from sides 68, 69 facing each other.

On the other hand, the arm construction comprising the above basic structure can be defined to be realized according to the invention such that said jointing is implemented such that at least the ends of the successive support arms 55, 56, 55', 56' are positioned substantially side by side, or such that the centre axis of the first support arm 55 moves on a plane which is substantially parallel but at a distance from a plane which is defined by the centre axis of the support arm 66 jointed to the first support arm 55 and an axis intersecting this axis and being at right angles with respect to said joint axis 60. Furthermore, the structure can be implemented such that the cabling required to use said radiation source 4 is arranged routed to the radiation source through at least the first and the second support arm supporting the radiation source and said jointing is implemented by a structure which connects the successive support arms substantially from the ends of the support arms such that a physical or virtual joint axis extending in the perpendicular direction with respect to the centre axes of the support arms and a route having dimensions enabling leading through of said cabling is formed at point, which route is substantially parallel with said joint axis and is located on said joint axis or in its substantial vicinity, or such that at least one support arm 56 comprises in connection with the side surface 69 of said support arm a structure 66 which coincides with the matching structure 62 arranged to the next support arm 55 such that either a rotation axis or part of a rotation axis is formed with respect to which the successive arm parts turn, or a route from a support arm to a second one is formed which is substantially parallel with said joint axis 60 and is located in the essential vicinity of said joint axis or coincides with it.

Further, the preferable embodiments of the invention include solutions in which the support arm 56 jointed to the first support arm 55 is jointed, substantially from the end opposite with respect to said jointing, to the next support arm 55' or some other structure such that a second physical or virtual joint axis substantially parallel with said joint axis 60 is formed, and in which at least one of the support arms 55, 56 comprises a cover, which is arranged to comprise a structure openable or detachable in the longitudinal direction of the support arm, said structure being substantially of the length of the support arm or covering at least a considerable portion of the length of the support arm and, on the other hand, solutions in which said structure openable or detachable in the longitudinal direction is implemented in connection with the support arm such that said structure is openable or detachable from the support arm without otherwise disassembling the arm construction.

In the arm construction, also the cabling required to use said radiation source 4 can be arranged to be routed to the radiation source 4 through at least the first and the second support arm supporting the radiation source and the jointing of the support arms implemented by a structure which connects the successive support arms substantially from the ends of the support arms such that in the structure in question a physical or virtual joint axis extending in the perpendicular direction with respect to the centre axes of the support arms is formed as well as a route having dimension enabling leading through of said cabling, which route is substantially parallel with said joint axis and is located on said joint axis and comprises a sleeve-like structure 62, 66 through which said cabling has been routed.

In the different embodiments of the invention, the successive support arms preferably comprise cover structures which include parts having a cross-section of the shape of a circle or part of a circular arch with substantially the same radius and which, when attached to each other, cover the jointing between the support arms in question and, advantageously, the furthest of the support arms with respect to the first support arm is attached to a horizontal arm, which is arranged to support the arm construction as a whole, which attachment is implemented by a structure enabling turning of the arm construction with respect to a vertical axis. The construction according to the invention enables implementation of the support arms as substantially identical or identical structures.

The invention claimed is:

1. An arm construction of an intra-oral x-ray device which comprises at least two elongated support arms including a first and a last elongated support arm, at least two of the elongated support arms rotatably connected to each other by a first jointing structure disposed on facing sidewalls of said elongated support arms rotatably connected to each other by the first jointing structure, the first elongated support arm including the first jointing structure and a radiation source connected thereto by a second jointing structure located substantially at an end of the first support arm which is opposite with respect to a location of said first jointing structure, and wherein the last elongated support arm includes the first jointing structure and is connected to a support structure of the arm construction by a connection located substantially at an end of the last support arm which is opposite with respect to said first jointing structure, said arm construction being configured such that said at least two elongated support arms are turnable with respect to a physical or virtual joint axis defined by said first jointing structure, wherein the first jointing structure rotatably connecting two of the at least two elongated support arms is configured such that ends of said two elongated support arms opposite said first jointing structure can be positioned substantially side by side, the construction further comprising at least one of:

the second jointing structure faces a sidewall of the first elongated support arm and the first and the second jointing structures on the first elongated support arm face in the same direction;

the connection on the last elongated support arm and the first jointing structure of the last elongated support arm face in the same direction; and at least one further elongated support arm between said first elongated support arm and said last elongated support arm includes said first jointing structure at one of its ends and a third jointing structure at an opposite end, and wherein said first and third jointing structures face in the same direction.

2. An arm construction of an intra-oral x-ray device, which comprises at least two elongated support arms rotatably connected to each other, each of said at least two elongated support arms having a centre axis and an elongated side surface, a radiation source substantially at an end of the first support arm which is opposite a jointing structure connecting a first and a second of the at least two elongated support arms, which jointing structure renders the first support arm turnable with respect to a physical or virtual joint axis defined by said jointing structure, wherein a cabling required to use said radiation source is arranged routed to the radiation source through at least the first and a second support arm of said at least two elongated support arms and said jointing structure is implemented by a structure which attaches successive support arms substantially from the ends of the support arms and comprises a spindle on one of said support arms and an axle on the other of said support arms receiving the spindle, said spindle and axle being housed within an outer surface of a respective one of said elongated support arms, and wherein said axle receives said spindle such that said spindle penetrates the elongated side surface of the elongated support arm housing the axle and intersects said centre axis, said spindle and axle in combination having a physical or virtual axis extending perpendicularly with respect to centre axes of the at least two elongated support arms, and wherein said spindle and axle in combination form a route receiving said cabling, which route is substantially parallel with said joint axis and is located on said joint axis or in its essential vicinity.

3. An arm construction of an intra-oral x-ray device, which comprises at least two elongated support arms rotatably connected to each other by a first jointing structure, a radiation source connected by a second jointing structure to an end of a first of said at least two elongated support arms which is opposite with respect to said first jointing structure rotatably connecting a first and a second of the at least two elongated support arms, which rotatable connectivity is configured such that the first support arm is turnable with respect to a physical or virtual joint axis defined by said jointing structure, wherein said first jointing structure comprises a spindle in connection with a side surface of at least one of the first and the second of the at least two support arms and a cooperative axle arranged to a side surface of the other of the first and second of the at least two support arms such that at least a partial rotation axis, and a cabling route between said at least elongated support arms is formed, which are substantially parallel with said joint axis and is located substantially in the vicinity of said joint axis or coincides with it and wherein said cabling route allows an associated cable to be fully housed within a length of the at least two support arms and said first jointing structure, and wherein the first support arm moves on a plane which is substantially parallel with a plane which is defined by a centre axis of the support arm connected to the first support arm and an axis which intersects said axis and is perpendicular with respect to said joint axis and which plane on which the first support arm moves is at such a distance from the above comparison plane that, if the first support arm is turned to any angle with respect to the support arm to which it is connected, none of the structures of these successive support arms touch each other.

4. An arm construction of an intra-oral x-ray device according to claim 2, wherein a centre axis of the first support arm moves on a plane which is substantially parallel but at a distance from a plane which is defined by the centre axis of the support arm rotatably connected to the first support arm and an axis which intersects this axis and is perpendicular with respect to said joint axis.

5. An arm construction according to claim 1, wherein the first support arm moves on a plane which is substantially parallel with a plane which is defined by a centre axis of the support arm connected to the first support arm and an axis which intersects said axis and is perpendicular with respect to said joint axis and which plane on which the first support arm moves is at such a distance from the above comparison plane that, if the first support arm is turned to any angle with respect to the support arm to which it is rotatably connected, none of the structures of these successive support arms touch each other.

6. An arm construction according to claim 2, wherein the support arm rotatably connected to the first support arm includes a further jointing structure, substantially at an end opposite with respect to the end connected to the first support arm, connecting to a further support arm or some other structure such that it forms a second physical or virtual joint axis substantially parallel with said joint axis.

7. An arm construction according to claim 2, wherein at least one of the support arms includes a cover which is arranged to comprise an openable or detachable structure in the longitudinal direction of the support arm, which structure is substantially a length of the support arm or covers at least a significant portion of the length of the support arm.

8. An arm construction according to claim 7, wherein said openable or detachable structure in the longitudinal direction is arranged in connection with the support arm such that the associated structure is openable or detachable from the support arm without otherwise disassembling the arm construction.

9. An arm construction according to claim 1, wherein cabling required to use said radiation source is routed to the radiation source through at least a first and a second support arm supporting the radiation source and said jointing structure which connects the successive support arms substantially from the ends of the support arms such that a physical or virtual joint axis extending in a perpendicular direction with respect to the centre axes of the support arms and defines a route with dimensions enabling leading through of said cabling, which route is substantially parallel with said joint axis and is located on said joint axis and comprises a sleeve-like structure through which said cabling has been routed.

10. An arm construction according to claim 2, wherein successive support arms include cover structures which include parts having a cross-section in the shape of a circle or part of a circular arch with substantially the same radius which, when connected to each other, cover the jointing structure between the associated support arms.

11. An arm construction according to claim 1, wherein at least one of the support arms is attached to a horizontal arm and wherein attachment is achieved by a structure enabling turning of the arm construction around a vertical axis.

12. An arm construction according to claim 1, wherein at least two of the support arms comprise at least substantially identical structures.

13. An arm construction according to claim 1, wherein the first support arm moves on a plane which is substantially parallel with a plane which is defined by a centre axis of the last support arm connected to the first support arm and an axis which intersects said axis and is perpendicular with respect to said joint axis and which plane on which the first support arm moves is at such a distance from the above comparison plane that, if the first support arm is turned to any angle with respect to the last support arm to which it is rotatably connected, none of the structures of these successive support arms touch each other.

14. An arm construction according to claim 2, wherein the first support arm moves on a plane which is substantially parallel with a plane which is defined by a centre axis of the support arm connected to the first support arm and an axis which intersects said axis and is perpendicular with respect to said joint axis and which plane on which the first support arm moves is at such a distance from the above comparison plane that, if the first support arm is turned to any angle with respect to the support arm to which it is rotatably connected, none of the structures of these successive support arms touch each other.

15. An arm construction according to claim 4, wherein the first support arm moves on a plane which is substantially parallel with a plane which is defined by the centre axis of the support arm connected to the first support arm and an axis which intersects said axis and is perpendicular with respect to said joint axis and which plane on which the first support arm moves is at such a distance from the above comparison plane that, if the first support arm is turned to any angle with respect to the support arm to which it is connected, none of the structures of these successive support arms touch each other.

16. An arm construction according to claim 1, wherein the last support arm rotatably connected to the first support arm is further rotatably connected, substantially from an end opposite to the rotatable connection with the first support arm, to a next support arm or some other structure such that it forms a second physical or virtual joint axis substantially parallel with said joint axis.

17. An arm construction according to claim 2, wherein the support arm rotatably connected to the first support arm is further rotatably connected, substantially from an end opposite to the rotatable connection with the first support arm, to a next support arm or some other structure such that it forms a second physical or virtual joint axis substantially parallel with said joint axis.

18. An arm construction according to claim 3, wherein the support arm rotatably connected to the first support arm is further rotatably connected, substantially from an end opposite to the rotatable connection with the first support arm, to a next support arm or some other structure such that it forms a second physical or virtual joint axis substantially parallel with said joint axis.

19. An intra-oral x-ray device comprising a radiation source supported by at least two elongated arms, said elongated arms including elongated sidewalls, said at least two elongated arms interconnected by a rotatable connection and having at least one orientation in which said elongated sidewalls are at least substantially overlapping when each is positioned vertically, said rotatable connection being formed on the elongated sidewalls of each of the at least two elongated arms, and wherein at least one of said at least two elongated arms includes a further rotatable connection on said elongated sidewall, said further rotatable connection being configured for mating with at least one of the radiation source, an additional elongated arm, and a support arm and wherein said rotatable connections are implemented such that the at least two elongated support arms connect to each other from sides facing each other.

* * * * *